United States Patent
El-Chafei et al.

(10) Patent No.: US 12,186,207 B2
(45) Date of Patent: Jan. 7, 2025

(54) ORTHOPEDIC INSTRUMENT FOR INSERTING A FEMORAL STEM

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Mouhsin Ahmad El-Chafei, Arlington, TN (US); Jacob Zimmerman, Memphis, TN (US); Marc Wright, Memphis, TN (US)

(73) Assignees: Smith & Nephew, Inc., Memphis, TN (US); Smith & Nephew Orthopaedics AG, Memphis, TN (US); Smith & Nephew Asia Pacific Pte. Limited, CH Singapore (SG)

( * ) Notice: Subject to any disclaimer, the term of this patent is extended or adjusted under 35 U.S.C. 154(b) by 343 days.

(21) Appl. No.: 17/705,285

(22) Filed: Mar. 26, 2022

(65) Prior Publication Data

US 2022/0323238 A1    Oct. 13, 2022

Related U.S. Application Data

(60) Provisional application No. 63/173,823, filed on Apr. 12, 2021.

(51) Int. Cl.
*A61F 2/46* (2006.01)
*A61F 2/36* (2006.01)
*A61F 2/30* (2006.01)

(52) U.S. Cl.
CPC ............ *A61F 2/4607* (2013.01); *A61F 2/367* (2013.01); *A61F 2002/30378* (2013.01); *A61F 2002/4681* (2013.01)

(58) Field of Classification Search
CPC ........ A61F 2/46; A61F 2/4603; A61F 2/4607; A61F 2/4612; A61F 2/4605; A61F 2/4606; A61F 2/461; A61B 17/56; A61B 17/8841; A61B 17/92
See application file for complete search history.

(56) References Cited

U.S. PATENT DOCUMENTS

| | | | | |
|---|---|---|---|---|
| 4,601,289 | A * | 7/1986 | Chiarizzio | A61B 17/1659 606/85 |
| 4,728,334 | A * | 3/1988 | Spotorno | A61F 2/30771 623/23.31 |
| 4,813,962 | A * | 3/1989 | Deckner | A61B 90/94 623/22.4 |

(Continued)

*Primary Examiner* — Alvin J Stewart
(74) *Attorney, Agent, or Firm* — KDW Firm PLLC

(57) ABSTRACT

An orthopedic instrument or inserter arranged and configured to insert, position (e.g., align), and remove, if necessary, an orthopedic implant (e.g., a femoral stem or implant). In one embodiment, the inserter and femoral stem are configured to enable the inserter to be quickly and easily coupled to the femoral stem via, for example, a quick-connect, non-threaded connection. Moreover, in one or more preferred embodiments, the inserter is configured to be angularly adjustable relative to the femoral stem. For example, the angular position of the inserter may be adjusted relative to the position of the femoral stem to accommodate different patient anatomy and/or various surgical approaches. In one embodiment, the inserter includes a ball-shaped head portion for coupling to a cavity formed in the femoral stem.

18 Claims, 15 Drawing Sheets

(56) References Cited

U.S. PATENT DOCUMENTS

| | | | | |
|---|---|---|---|---|
| 5,171,275 | A * | 12/1992 | Ling | A61F 2/468 |
| | | | | 128/898 |
| 5,456,717 | A * | 10/1995 | Zweymuller | A61F 2/367 |
| | | | | 623/23.15 |
| 5,476,466 | A * | 12/1995 | Barrette | A61F 2/4607 |
| | | | | 606/86 R |
| 5,849,015 | A | 12/1998 | Haywood et al. | |
| 6,126,659 | A * | 10/2000 | Wack | A61F 2/4601 |
| | | | | 606/60 |
| 6,190,416 | B1 * | 2/2001 | Choteau | A61B 17/1668 |
| | | | | 606/85 |
| 6,626,913 | B1 * | 9/2003 | Mckinnon | A61F 2/367 |
| | | | | 606/86 R |
| 7,998,147 | B2 * | 8/2011 | Santarella | A61F 2/4607 |
| | | | | 623/22.12 |
| 9,084,685 | B2 * | 7/2015 | Huff | A61F 2/367 |
| 2004/0010262 | A1 * | 1/2004 | Parkinson | A61F 2/4607 |
| | | | | 606/99 |
| 2004/0153082 | A1 * | 8/2004 | Howie | A61F 2/4601 |
| | | | | 606/86 R |
| 2005/0203536 | A1 * | 9/2005 | Laffargue | A61B 34/20 |
| | | | | 606/91 |
| 2005/0203539 | A1 * | 9/2005 | Grimm | A61F 2/4607 |
| | | | | 606/99 |
| 2005/0234470 | A1 * | 10/2005 | Hershberger | A61F 2/4637 |
| | | | | 623/908 |
| 2009/0099566 | A1 | 4/2009 | Maness et al. | |
| 2009/0112209 | A1 * | 4/2009 | Parrott | A61B 17/1717 |
| | | | | 606/62 |
| 2012/0296339 | A1 * | 11/2012 | Iannotti | A61B 17/1703 |
| | | | | 606/86 R |
| 2015/0182341 | A1 * | 7/2015 | Slater | A61F 2/4607 |
| | | | | 623/23.15 |
| 2021/0353430 | A1 * | 11/2021 | Atkin | A61F 2/4607 |
| 2022/0061997 | A1 * | 3/2022 | Conrad | A61B 17/92 |
| 2022/0354559 | A1 * | 11/2022 | Lashure | A61F 2/4609 |
| 2023/0355409 | A1 * | 11/2023 | Brazil | A61F 2/367 |

* cited by examiner

ORTHOPEDIC INSTRUMENT FOR INSERTING A FEMORAL STEM

CROSS-REFERENCE TO RELATED APPLICATIONS

This is a non-provisional of, and claims the benefit of the filing date of, pending U.S. provisional patent application No. 63/173,823, filed Apr. 12, 2021, entitled "Orthopedic Instrument for Inserting a Femoral Stem," the entirety of which application is incorporated by reference herein.

TECHNICAL FIELD

The present disclosure is directed to an orthopedic instrument or inserter, and more specifically to an orthopedic instrument or inserter arranged and configured to manipulate (e.g., insert, position (e.g., align), and remove, if necessary) an orthopedic implant (e.g., a femoral stem or implant).

BACKGROUND

Total hip arthroplasty or hip replacement is a well-known procedure for repairing damaged bone (e.g., a damaged hip). During a total hip arthroplasty, precise implantation of an intramedullary stem (e.g., a femoral stem or implant) is needed. To assist with insertion, positioning (e.g., alignment), and removal, if necessary, of the femoral stem, instruments have been developed to align and impact the stem into the femoral canal of the patient's bone.

Generally speaking, in use, the instrument or inserter is coupled to the femoral stem and is arranged and configured to guide, align, etc. the femoral stem into the patient's bone. In addition, the inserter may be arranged and configured to be impacted to insert, drive, etc. the femoral stem into the patient's bone.

One disadvantage of current inserters is that the connection mechanism used to couple the inserter to the femoral stem is fixed. That is, current inserters generally utilize a threaded connection between the inserter and the femoral stem. Alternatively, slots, keyways, etc. have been used to couple the inserter to the femoral stem. However, in either implementation, the connection mechanism between the inserter and the femoral stem is fixed. That is, the connection mechanism does not enable any degree of angulation or adjustment between the inserter and the femoral stem. As such, the connection mechanism does not enable angular adjustments for the patient's anatomy and/or surgical procedure. In addition, threaded couplings or connections between the inserter and the femoral stem reduce the impaction strength of the system as one must be concerned with damaging and/or breaking the threads.

To overcome this deficiency, orthopedic manufacturers have generally provided a variety of different inserters with each inserter arranged and configured for a particular surgical procedure. For example, different surgical approaches, such as a posterior approach or a direct anterior approach, directly affect the inserter and connection mechanism by limiting space or access points along the surgical table. Moreover, additional challenges are faced when different approaches are paired with smaller sized femoral stems, which limit the features that can be utilized. This also limits the size and functionality of the inserter.

Thus, it would be beneficial to provide an inserter incorporating a connection mechanism that enables angular adjustment between the inserter and the femoral stem to accommodate different patient anatomy and/or different surgical approaches.

It is with this in mind that the present disclosure is provided.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Disclosed herein is an orthopedic instrument or inserter arranged and configured to manipulate (e.g., insert, position (e.g., align), and remove, if necessary) an orthopedic implant such as, for example, a femoral stem. In one embodiment, the inserter and femoral stem are configured to enable the inserter to be quickly and easily coupled to the femoral stem via, for example, a quick-connect, non-threaded connection. Moreover, in one or more preferred embodiments, the inserter is arranged and configured to be angularly adjustable relative to the femoral stem even after the inserter has been coupled to the femoral stem. For example, the angular position of the inserter may be adjusted relative to the position of the femoral stem to accommodate different patient anatomy and/or various surgical approaches. In one embodiment, the inserter includes an enlarged head portion (e.g., a spherical or ball-shaped head portion) for coupling to a cavity formed in the femoral stem. Thus arranged, for example, the position of the inserter such as, for example, the medial-lateral position and/or the rotational position of the inserter in the Z-axis may be adjusted relative to the femoral stem.

In one embodiment, an orthopedic system for total hip arthroplasty is disclosed. The system comprising a femoral stem and an inserter arranged and configured to couple to the femoral stem to facilitate insertion of the femoral stem within an intramedullary canal of a patient's bone, the inserter including a quick-connect, non-threaded connection for coupling, engaging, etc. the femoral stem.

In one embodiment, after coupling the inserter to the femoral stem (e.g., in use, with the inserter coupled to the femoral stem), the inserter is arranged and configured to be angularly adjustable relative to the femoral stem. For example, the medial-lateral position of the inserter and/or the rotational position of the inserter in the Z-axis may be adjusted relative to the femoral stem.

In one embodiment, the femoral stem includes a cavity. The inserter includes an enlarged head portion (e.g., a spherical or ball-shaped head portion) extending from a distal end of the inserter, the head portion being arranged and configured to be received within the cavity of the femoral stem to couple the inserter to the femoral stem while enabling an orientation of the inserter to be angularly adjustable relative to the femoral stem. For example, the medial-lateral position of the inserter and/or the rotational position of the inserter in the Z-axis may be adjusted relative to the femoral stem.

In one embodiment, the inserter includes a body portion and a reduced diameter rod extending from the body portion, the ball-shaped head portion being arranged at a distal end of the reduced diameter rod.

In one embodiment, the cavity includes a ramped pathway in communication with a pocket. The ramped pathway being arranged and configured to guide the ball-shaped head portion into the pocket.

In one embodiment, the ball-shaped head portion is inserted into the pocket by inserting the ball-shaped head portion along the ramped pathway until the ball-shaped head portion reaches a distal end of the ramped pathway and then moving the ball-shaped head portion laterally into the pocket.

In one embodiment, the cavity is arranged and configured to prevent the ball-shaped head portion from being axially pulled out of the pocket.

In one embodiment, the pocket includes an inwardly extending ledge arranged and configured to prevent the ball-shaped head portion from being axially pulled out of the pocket.

In one embodiment, the pocket includes a smaller diameter cross-sectional area at a proximal end thereof arranged and configured to prevent the ball-shaped head portion from being axially pulled out of the pocket.

In one embodiment, the ball-shaped head portion includes a key arranged and configured to engage a corresponding recess formed in the pocket of the femoral stem, engagement of the key and the recess preventing angular adjustment of the inserter relative to the femoral stem. That is, in one embodiment, engagement of the key with the recess may prevent, or at least inhibit, rotational movement of the inserter about the Z-axis while enabling the medial-lateral position of the inserter to be adjusted relative to the femoral stem.

In one embodiment, the head portion is in a form of a semi-round head portion including a straight lateral side surface for interacting with a straight surface formed in the pocket, interaction between the straight lateral side surface and the straight surface preventing angular adjustment of the inserter relative to the femoral stem. That is, in one embodiment, interaction of the surfaces may prevent, or at least inhibit, rotational movement of the inserter about the Z-axis while enabling the medial-lateral position of the inserter to be adjusted relative to the femoral stem.

In one embodiment, the inserter includes a body portion and an extension rod extending from the body portion, the head portion being arranged at a distal end of the rod, the extension rod including a square or substantially square cross-sectional profile, the extension rod being arranged and configured to interact with the pocket to prevent angular adjustment of the inserter relative to the femoral stem. That is, in one embodiment, interaction of the extension rod and pocket may prevent, or at least inhibit, rotational movement of the inserter about the Z-axis while enabling the medial-lateral position of the inserter to be adjusted relative to the femoral stem.

In one embodiment, the inserter includes a T-shaped coupler or end-portion formed at a distal end thereof, and the femoral stem includes a corresponding cavity arranged and configured to receive the T-shaped coupler or end-portion, in use, rotation of the inserter relative to the femoral stem couples the inserter to the femoral stem.

A method for coupling an orthopedic inserter to a femoral stem is also disclosed. In one embodiment, the inserter includes a ball-shaped head portion formed at a distal end thereof. The inserter includes a cavity arranged and configured to receive the ball-shaped head portion. The method includes inserting a ball-shaped head portion formed at a distal end of the orthopedic inserter into a cavity formed in the femoral stem. Inserting the ball-shaped head portion into the cavity includes positioning the ball-shaped head portion into the cavity adjacent to a ramped pathway, inserting the ball-shaped head portion into the cavity along the ramped pathway, laterally moving the ball-shaped head portion into a pocket, and tilting the inserter relative to the femoral stem.

In one embodiment, the pocket includes a ledge extending therein, the ledge being arranged and configured to prevent the ball-shaped head portion from being axially pulled out of the pocket.

In one embodiment, inserting the ball-shaped head portion into the cavity along the ramped pathway includes positioning the ball-shaped head portion distally, beneath the ledge.

In one embodiment, laterally moving the ball-shaped head portion to a pocket includes laterally moving the ball-shaped head portion laterally beneath the ledge.

In one embodiment, decoupling the inserter from the femoral stem further includes laterally moving the ball-shaped head portion from beneath the ledge toward the ramped pathway and axially withdrawing the ball-shaped head portion from the cavity along the ramped pathway.

In one embodiment, an implant such as, for example, a femoral stem including a cavity arranged and configured to receive an inserter (e.g., an enlarged head portion such as, for example, a spherical or ball-shaped head portion of an inserter) is disclosed. In one embodiment, the cavity formed in the femoral stem is arranged and configured to enable insertion and removal of the inserter (e.g., ball-shaped head portion) when the ball-shaped head portion of the inserter is positioned or aligned with a first portion of the cavity (e.g., a ramped pathway). The cavity being arranged and configured to prevent decoupling or removal of the ball-shaped head portion when the ball-shaped head portion of the inserter is positioned or aligned with a second portion of the cavity (e.g., pocket).

In one embodiment, the second portion of the cavity includes an inwardly extending ledge, projection, dimple, shelf, etc. for preventing decoupling or removal of the inserter when the ball-shaped head portion is positioned in the second portion of the cavity. In one embodiment, the second portion of the cavity is arranged and configured to receive the ball-shaped head portion of the inserter laterally, but is arranged and configured to prevent the ball-shaped head portion of the inserter from being removed axially.

In one embodiment, the first portion of the cavity includes an insertion/extraction slot or pathway (e.g., the ramped pathway). The second portion of the cavity includes a pocket including, for example, an inwardly extending ledge. In one embodiment, the insertion/extraction slot or pathway includes an angled, ramped, or tilted platform or surface. In use, the insertion/extraction slot or pathway leads to the pocket formed in the femoral stem. That is, in use, the insertion/extraction slot or pathway is arranged and configured to guide the ball-shaped head portion into the pocket, and thus into engagement with the femoral stem.

In one embodiment, the pocket is arranged and configured to receive the ball-shaped head portion so that the inserter is fixedly coupled to the femoral stem when the inserter is positioned within the pocket.

In one embodiment, the pocket is arranged and configured to enable the inserter to articulate relative to the femoral stem.

In one embodiment, the inserter may be coupled to the femoral stem by aligning the ball-shaped head portion adjacent to the first portion of the cavity (e.g., insertion/extraction slot or pathway). Thereafter, the ball-shaped head portion may be inserted, reduced, pushed, etc. along the first portion of the cavity (e.g., insertion/extraction slot or pathway) until the ball-shaped head portion reaches a distal end (e.g., bottom) of the first portion of the cavity (e.g., insertion/extraction slot or pathway). Next, the ball-shaped head portion may be moved (e.g., slid) laterally into the second portion of the cavity (e.g., the ball-shaped head portion may be moved laterally into the pocket). Thereafter, the rotational and/or angular position of the inserter may be adjusted as needed.

In use, the femoral stem is positioned relative to the patient's bone. Next, the inserter may be used to insert the femoral stem into the patient's bone. For example, in one embodiment, the surgeon may strike (e.g., hammer, etc.) a proximal end of the inserter to insert the femoral stem into the patient's bone (e.g., a surgeon may insert the femoral stem into the patient's bone via impacting a proximal end of the inserter (e.g., a pad connected to the inserter)).

In one embodiment, the cavity is formed in a proximal end of the femoral stem.

In one embodiment, the inserter may be coupled to the femoral stem during the surgical procedure on, for example, a surgical table.

Alternatively, in cases where a femoral stem needs to be removed from a patient's bone, the inserter may be coupled to the femoral stem by aligning the ball-shaped head portion adjacent to the first portion of the cavity (e.g., insertion/extraction slot or pathway) formed in the implanted femoral stem. Thereafter, the ball-shaped head portion may be inserted, reduced, pushed, etc. along the first portion of the cavity (e.g., insertion/extraction slot or pathway) until the ball-shaped head portion reaches a distal end (e.g., bottom) of the first portion of the cavity (e.g., insertion/extraction slot or pathway). Next, the ball-shaped head portion may be moved (e.g., slid) laterally into the second portion of the cavity (e.g., the ball-shaped head portion may be moved laterally into the pocket). The position of the inserter may be adjusted as needed. Thereafter, in use, the surgeon may strike (e.g., hammer, etc.) an underside of the pad associated with a proximal end of the inserter to remove the femoral stem from the patient's bone.

Embodiments of the present disclosure provide numerous advantages. For example, the inserter facilitates a rigid coupling between the inserter and the femoral stem while accommodating various surgical approaches, easier connection, increased insertion strength due to minimal force losses coming from a threaded connection (e.g., elimination of threads enables increased driving force (e.g., hammering) by eliminating the concern that the threads may break), ease of use, and/or a smaller needed surgical incision.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which.

Figure 1A:
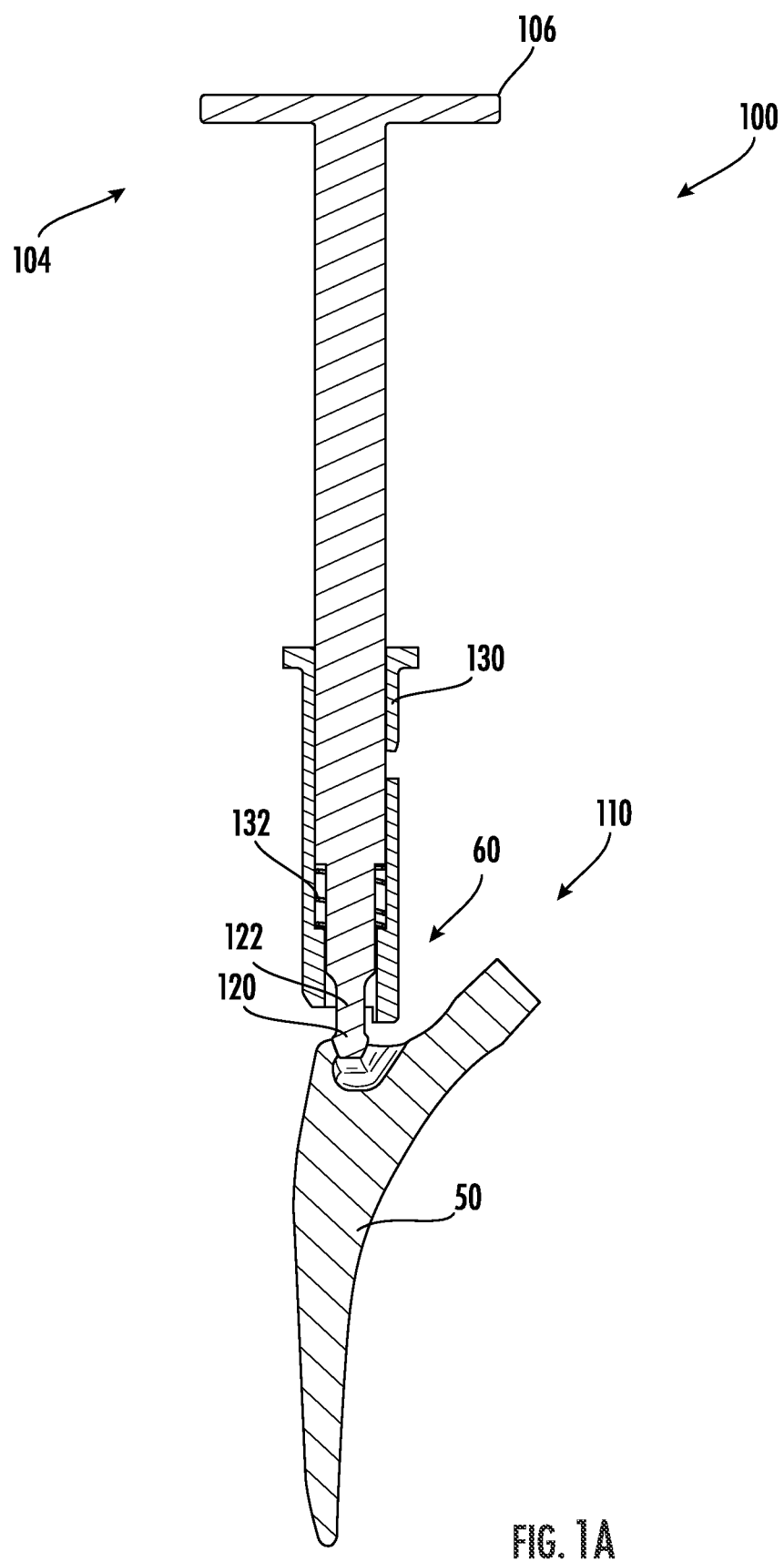
FIGS. 1A-1J illustrate various views of an example embodiment of an inserter being coupled to a femoral stem in accordance with one or more features of the present disclosure.

It should be understood that the drawings are not necessarily to scale and that the disclosed embodiments are sometimes illustrated diagrammatically and in partial views. In certain instances, details which are not necessary for an understanding of the disclosed methods and devices or which render other details difficult to perceive may have been omitted. It should be further understood that this disclosure is not limited to the particular embodiments illustrated herein. In the drawings, like numbers refer to like elements throughout unless otherwise noted.

DETAILED DESCRIPTION

Various features or the like of an orthopedic instrument or inserter (terms used interchangeably herein) arranged and configured to manipulate (e.g., insert, position (e.g., align), and remove, if necessary) an orthopedic implant such as, for example, a femoral stem or femoral implant (terms used interchangeably herein) will now be described more fully hereinafter with reference to the accompanying drawings, in which one or more features of the inserter will be shown and described. It should be appreciated that the various features may be used independently of, or in combination, with each other. It will be appreciated that an inserter as disclosed herein may be embodied in many different forms and should not be construed as being limited to the embodiments set forth herein. Rather, these embodiments are provided so that this disclosure will convey certain features of the inserter to those skilled in the art.

As will be described herein, in accordance with one or more features of the present disclosure, the inserter and femoral stem include various corresponding features arranged and configured to enable the inserter to be quickly and easily coupled to the femoral stem via, for example, a quick-connect, non-threaded connection. In addition, in one or more embodiments, the inserter is preferably arranged and configured to be angularly adjustable relative to the femoral stem. For example, the angular position of the inserter may be adjusted relative to the position of the femoral stem to accommodate different patient anatomy and/or various surgical approaches. That is, for example, in one embodiment, the medial-lateral position of the inserter and/or the rotational position of the inserter in the Z-axis may be adjusted relative to the femoral stem. Alternatively, in one embodiment, the medial-lateral position of the inserter relative to the femoral stem may be adjusted while, in a fully engaged position, the rotational position of the inserter in the Z-axis relative to the femoral stem may be fixed.

It should be appreciated that while various images of a femoral stem are shown, the present disclosure is directed to the connection or coupling between an orthopedic instrument or inserter and an orthopedic implant or femoral stem, thus the present disclosure should not be limited to any particular implant or femoral stem unless explicitly claimed.

Referring to FIGS. 1A-1J, in one embodiment, an inserter 100 in accordance with one or more features of the present disclosure is illustrated. As best illustrated in FIG. 1A, in one embodiment, the inserter 100 includes a proximal end 104 and a distal end 110. As illustrated, the proximal end 104 includes a pad 106. The distal end 110 includes an enlarged head portion such as, for example, a spherical or ball-shaped head portion 120 (collectively referred to herein as ball-shaped head portion). In use, as will be described in greater detail below, with the inserter 100 coupled to the femoral stem 50 and with the femoral stem 50 properly positioned relative to the patient's bone, a surgeon may strike (e.g., hammer, etc.) the pad 106 associated with the proximal end 104 of the inserter 100 to insert, drive, etc. the femoral stem 50 into the patient's bone. Alternatively, in cases where the femoral stem 50 needs to be removed from a patient's bone, the inserter 100 may be coupled to the femoral stem 50. Thereafter, in use, the surgeon may strike (e.g., hammer, etc.) an underside of the pad 106 associated with the proximal end 104 of the inserter 100 to remove the femoral stem 50 from the patient's bone.

In one embodiment, the inserter 100 may also include an outer body or sleeve 130 (terms used interchangeably herein) and a biasing member or spring 132 (terms used interchangeably herein). In use, the spring 132 is arranged and configured to enable the user to pull the sleeve 130 back (e.g., proximally) and rotate itself along a guided path such as, for example, a j-slot path. Thus, allowing a rotational stabilizing feature on the sleeve 130 to shift out of path to allow the ball-shaped head portion 120 to slide out of the femoral stem 50. In use, the incorporation of the sleeve 130 and the spring 132 assist with disassembly of the inserter 100 from the femoral stem 50.

In one embodiment, as illustrated, the inserter 100 may include a reduced diameter extension or rod 122 at the distal end 110 of the inserter 100, the ball-shaped head portion 120 being positioned at a distal end of the extension or rod 122 (e.g., the inserter may include a body portion and a reduced diameter extension or rod 122 extending from the body portion, the ball-shaped head portion 120 being arranged at a distal end of the extension or rod 122). In addition, as illustrated, the ball-shaped head portion 120 may include an enlarged diameter relative to the extension or rod 122.

As illustrated, the femoral stem 50 may include a cavity 60 formed in a proximal end thereof. The cavity 60 being arranged and configured to receive the ball-shaped head portion 120 of the inserter 100. In one embodiment, the cavity 60 includes first and second portions. For example, as illustrated, the cavity 60 may include an angled, ramped, or tilted platform or surface (e.g., an insertion/extraction slot or pathway) 62 leading to a pocket 64 for receiving the ball-shaped head portion 120 of the inserter 100. Thus arranged, in use, the ball-shaped head portion 120 may be easily positioned, guided, etc. by the surgeon into the pocket 64 via the ramped pathway 62, and thus into engagement with the femoral stem 50. Moreover, thus arranged, the inserter 100 need not be axially aligned with the femoral stem 50 during insertion (e.g., impaction) as off-axis impaction is enabled. In one embodiment, the cavity 60 and/or the pocket 64 may include a cylindrical shape or the like for receiving and interacting with the ball-shaped head portion 120.

Figure 1B:
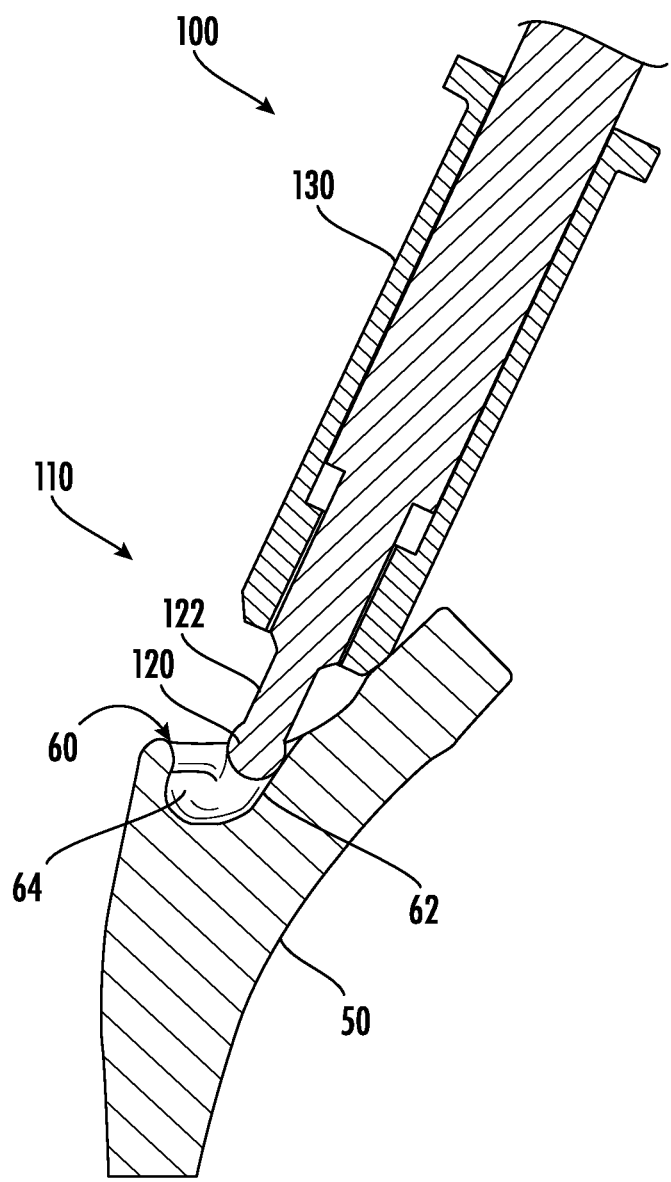
Figure 1C:
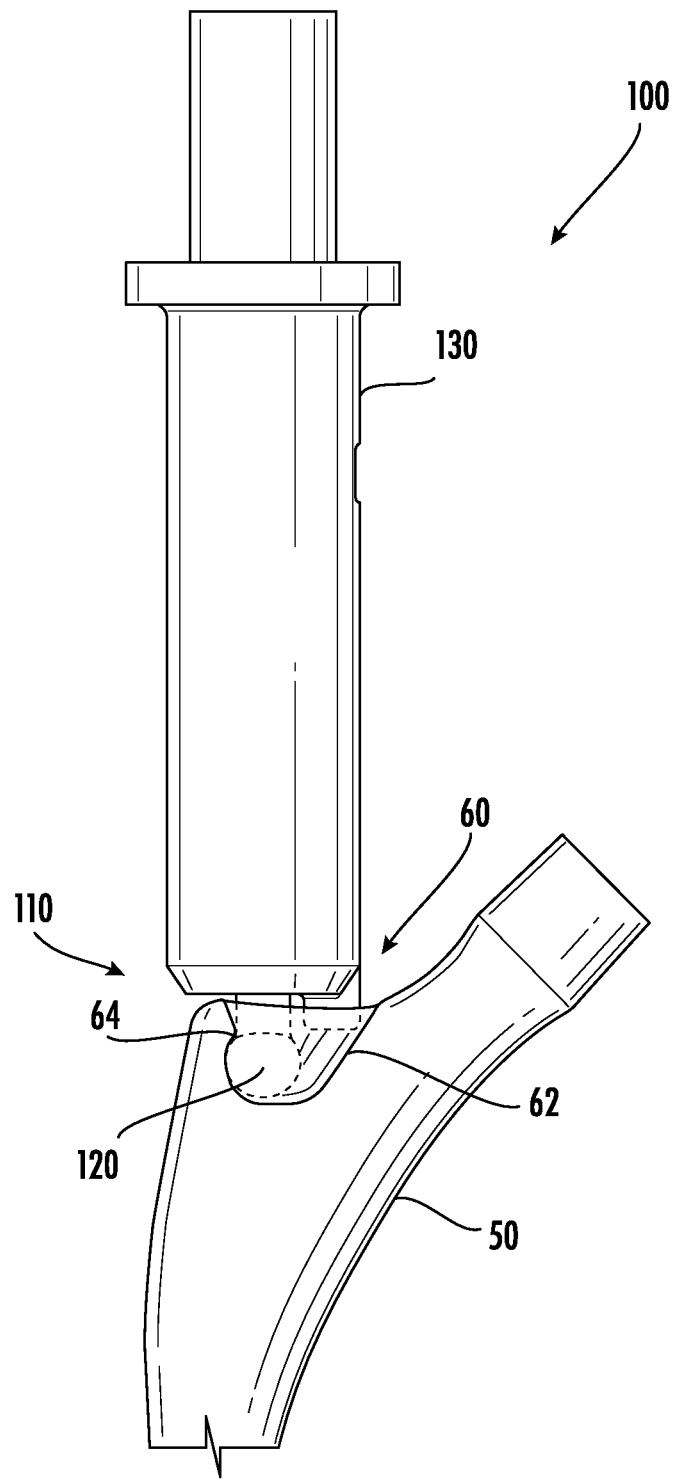
Figure 1D:
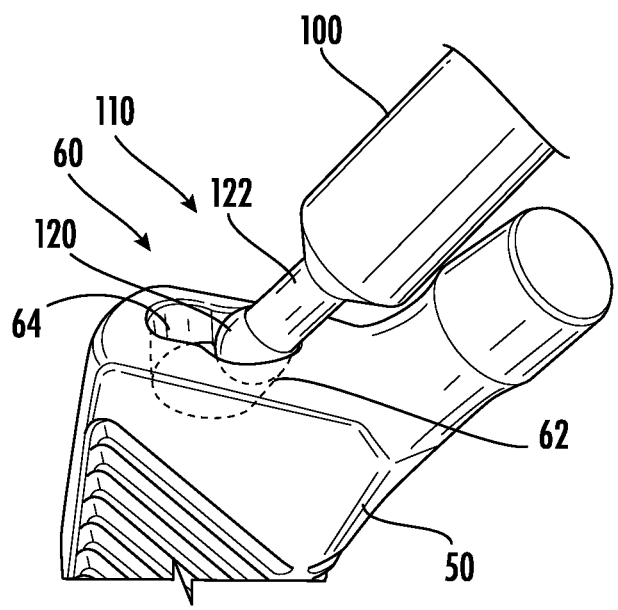
Figure 1E:
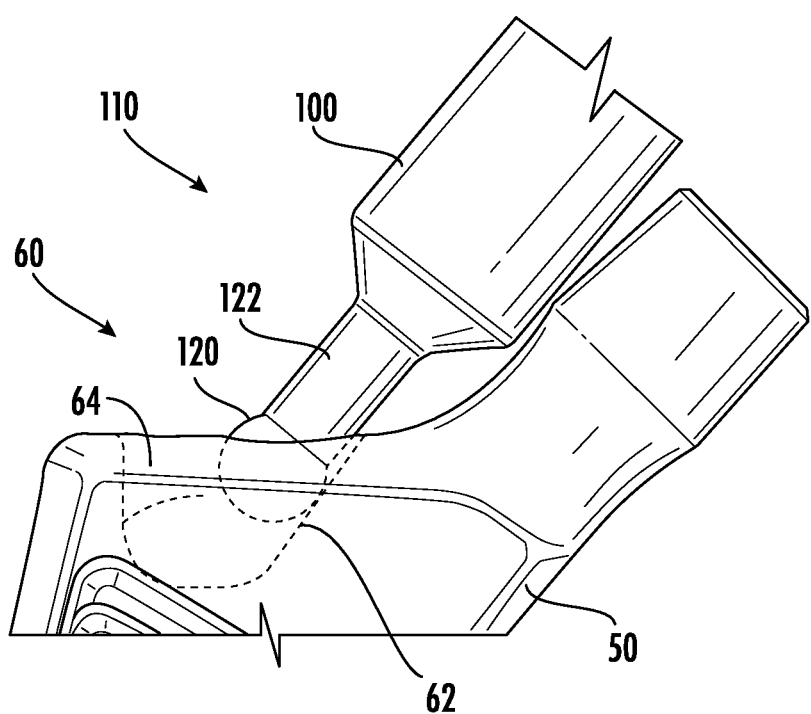
Figure 1F:
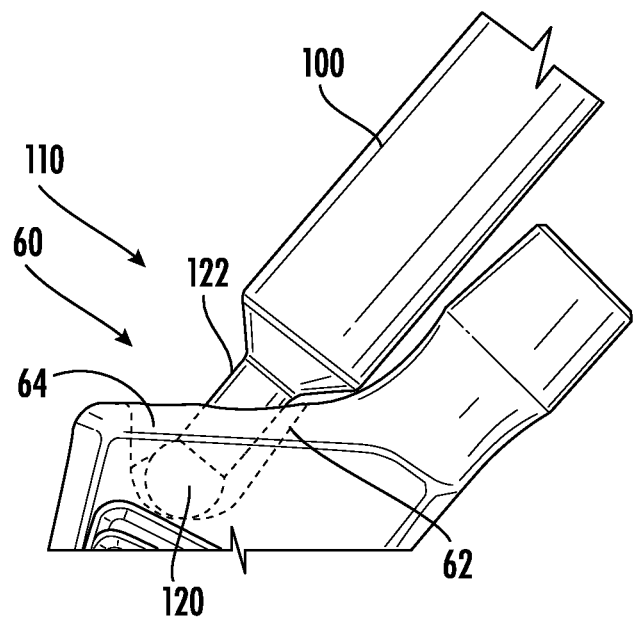
Figure 1G:
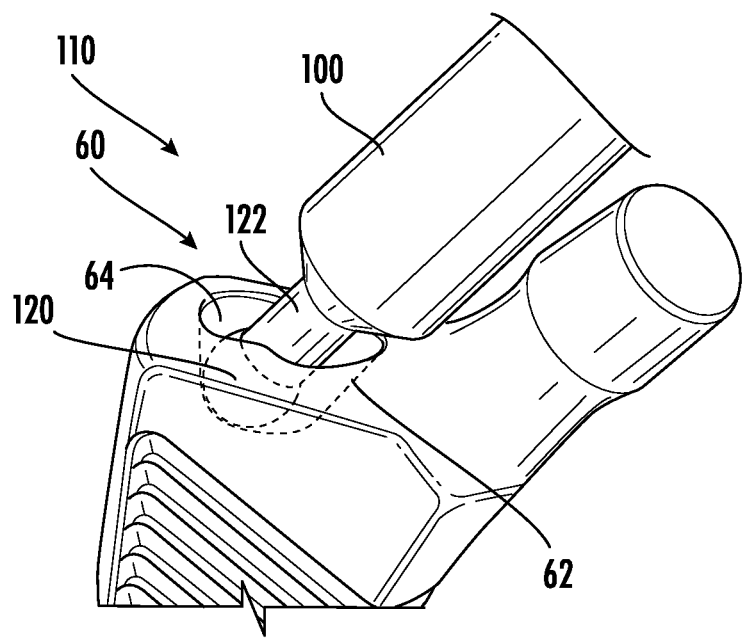

In use, referring to FIGS. 1B, 1D, and 1E, the inserter 100 may be coupled to the femoral stem 50 by positioning the ball-shaped head portion 120 of the inserter 100 into the cavity 60 formed in the femoral stem 50 adjacent to the ramped pathway 62. Thereafter, the ball-shaped head portion 120 may be inserted, reduced, pushed, etc. along the ramped pathway 62 until the ball-shaped head portion 120 reaches a distal end (e.g., bottom) of the ramped pathway 62. Next, as generally illustrated in FIGS. 1F and 1G, the ball-shaped head portion 120 may be moved (e.g., slid) laterally into the pocket 64 of the cavity 60 (e.g., the ball-shaped head portion 120 may be moved laterally into the pocket 64). Finally, referring to FIGS. 1H and 1I, the position of the inserter 100 may be rotationally and/or angularly adjusted relative to the femoral stem 50. For example, the inserter 100 may be tilted upright relative to the femoral stem 50. Thus arranged, in one embodiment, the ramped pathway 62 leads to the pocket 64 (e.g., cylindrical pocket) enabling the inserter 100 to be fixedly coupled to the femoral stem 50 without threads and regardless of surgical approach being used.

Figure 1H:
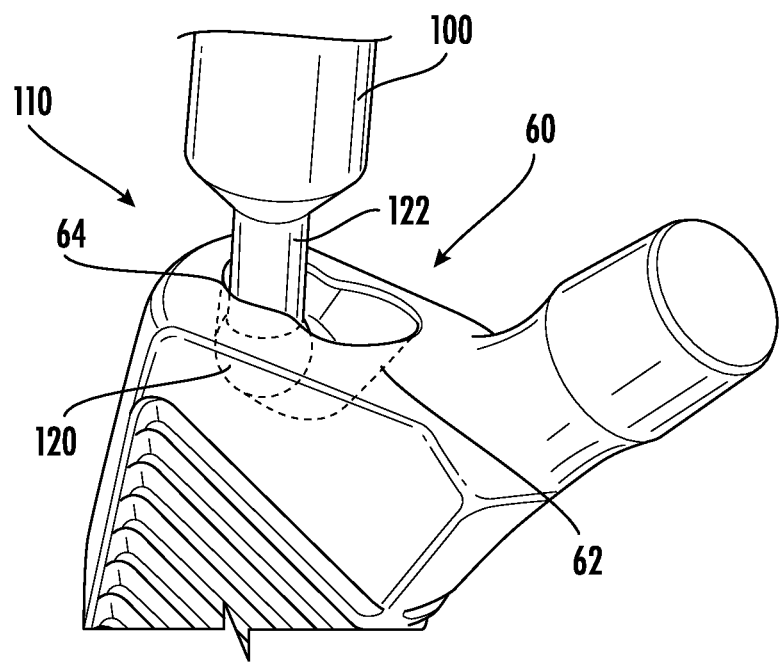
Figure 1I:
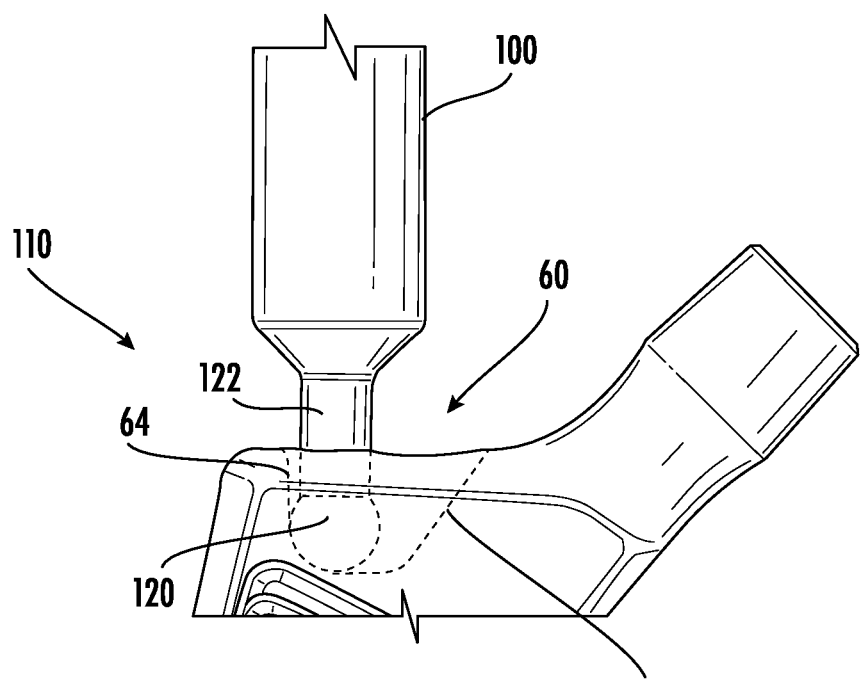
Figure 1J:
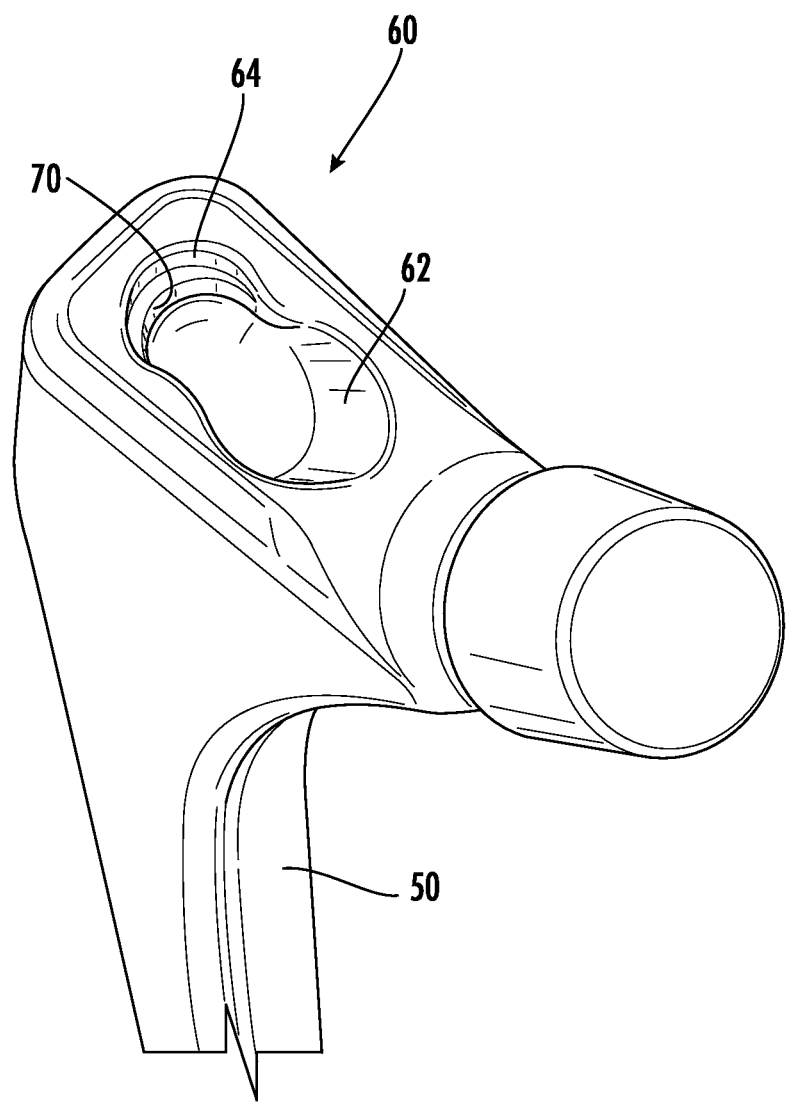

Once properly positioned within the pocket 64 as illustrated in FIGS. 1C, 1H, and 1I, the ball-shaped head portion 120 may be prevented from removal (e.g., decoupling) from the femoral stem 50. For example, the pocket 64 may be arranged and configured to prevent the ball-shaped head portion 120 from being accidentally disconnected from the femoral stem 50 via an axial motion. That is, referring to FIG. 1J, the pocket 64 may include an inwardly extending ledge, projection, a dimple, shelf, etc. 70 that is arranged and configured to prevent the ball-shaped head portion 120 from being pulled out axially (e.g., the pocket 64 is arranged and configured to prevent the ball-shaped head portion 120 from being pulled out axially, to remove the ball-shaped head portion 120 from the pocket 64, the ball-shaped head portion 120 must first be moved laterally out of the pocket 64 back towards the ramped pathway 62). That is, in use, in one embodiment, in order to couple and decouple the inserter 100 to and from the femoral stem 50, the ball-shaped head portion 120 must be initially positioned below the level of the ledge 70 and then laterally moved beneath the ledge 70.

It should be appreciated that the ball-shaped head portion 120 may be maintained within the pocket 64 via other now known or hereafter developed mechanisms. For example, in one embodiment, the pocket 64 may include a smaller diameter cross-sectional area at a proximal end thereof that is arranged and configured to prevent the ball-shaped head portion 120 from being removed until it is laterally positioned towards the ramped pathway 62.

Thus arranged, in use, by coupling the inserter 100 to the femoral stem 50 utilizing a ball-shaped head portion 120 and a corresponding cavity 60, the inserter 100 may be fixedly coupled to the femoral stem 50 to facilitate insertion, alignment, and/or removal of the femoral stem 50 as needed while enabling a position of the inserter 100 to be angularly adjusted relative to the femoral stem 50 so that the position of the inserter 100 can be orientated as needed in, for example, the medial-lateral position and/or the rotational position in the Z-axis, to suit the needs of the surgeon depending on, for example, the patient's anatomy and/or the type of surgical procedure being performed. The ramped pathway 62 and the pocket 64 enabling insertion of the ball-shaped head portion 120 to sit in the corresponding pocket 64 to facilitate easy coupling of the inserter 100 to the femoral stem 50.

It should be appreciated that while the inserter 100 has been described as including a ball-shaped head portion 120 and the femoral stem 50 has been described as including a corresponding cavity 60 to facilitate easier coupling and/or angular adjustment of the inserter 100 relative to the femoral stem 50, it should be appreciated that the present disclosure should not be so limited and that other mechanisms to facilitate easier coupling and/or angular adjustment of the inserter 100 relative to the femoral stem 50 may be used. For example, a semi-spherical and semi-rectangular tip, a spherical tip with a square shaft for rotational purposes, a hexagonal tip, a square tip, a separate body for rotational stability, variable angle ramps, etc.

In addition, in some embodiments, the inserter and femoral stem may be arranged and configured with an anti-rotational mechanism to prevent the inserter from rotating about the femoral stem when the inserter is coupled to the femoral stem. That is, in use, the inserter and femoral stem may include an anti-rotational mechanism to control rotation of the inserter and femoral stem about, for example, the Z-axis. Thus arranged, the inserter is prevented from rotating relative to the femoral stem about the Z-axis when the inserter is fully seated within the cavity of the femoral stem.

In accordance with one or more features of the present disclosure, in use, to insert an implant such as, for example, the femoral stem 50, the inserter 100 may be coupled to the femoral stem 50 by aligning the ball-shaped head portion 120 with the ramped pathway 62. Thereafter, the ball-shaped head portion 120 may be inserted, reduced, pushed, etc. along the ramped pathway 62 until the ball-shaped head portion 120 reaches a distal end (e.g., bottom) of the ramped pathway 62. Next, the ball-shaped head portion 120 may be moved (e.g., slid) laterally into the pocket 64 (e.g., the ball-shaped head portion 120 may be moved laterally into the pocket 64 so that the ball-shaped head portion 120 is positioned beneath the inwardly extending ledge 70 so that the ball-shaped head portion 120 is prevented from being removed from the cavity 60). Thereafter, the rotational and/or angular position or alignment of the inserter 100 may be adjusted relative to the femoral stem 50 and/or patient as needed. Thereafter, with the femoral stem 50 properly positioned relative to the patient's bone, the inserter 100 may be used to insert the femoral stem 50 into the patient's bone. For example, in one embodiment, the surgeon may strike (e.g., hammer, etc.) the pad 106 associated with the proximal end 104 of the inserter 100.

Alternatively, in cases where an implant such as, for example, the femoral stem 50, needs to be removed from a patient's bone, the inserter 100 may be coupled to the femoral stem 50 by aligning the ball-shaped head portion 120 with the ramped pathway 62 formed in the implanted femoral stem 50. Thereafter, the ball-shaped head portion 120 may be inserted, reduced, pushed, etc. along the ramped pathway 62 until the ball-shaped head portion 120 reaches a distal end (e.g., bottom) of the ramped pathway 62. Next, the ball-shaped head portion 120 may be moved (e.g., slid) laterally into the pocket 64 so that the ball-shaped head portion 120 is positioned beneath the inwardly extending ledge 70 so that the ball-shaped head portion 120 is prevented from being removed from the cavity 60. Thereafter, the rotational and/or angular position or alignment of the inserter 100 may be adjusted relative to the femoral stem 50 and/or patient as needed. Thereafter, the surgeon may strike (e.g., hammer, etc.) an underside of the pad 106 associated with the proximal end 104 of the inserter 100 to remove the femoral stem 50 from the patient's bone.

Figure 2A:
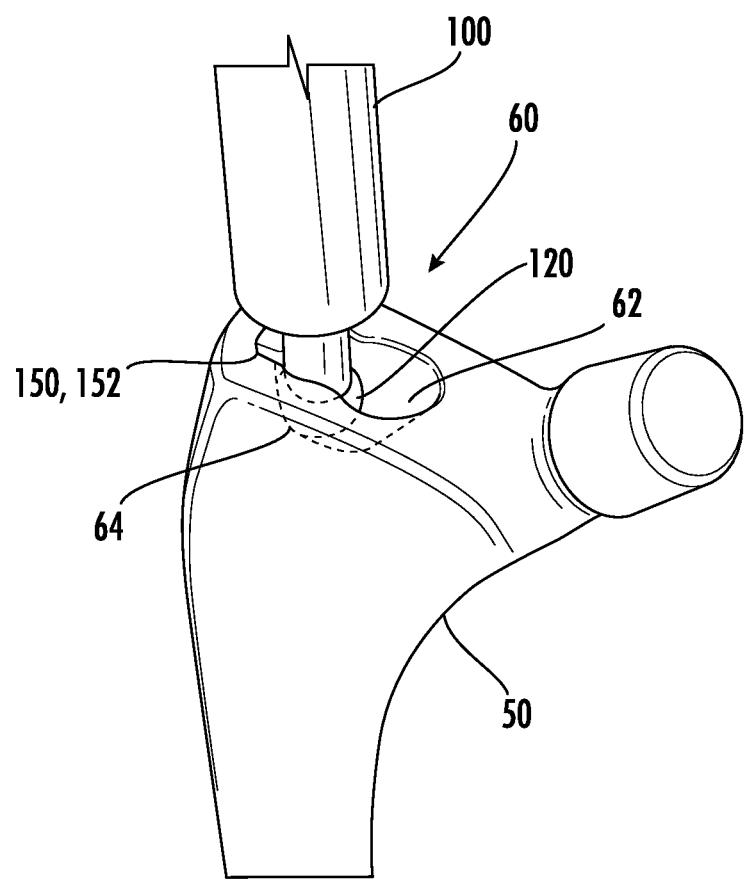
FIGS. 2A and 2B illustrate various views of another example embodiment of an inserter being coupled to a femoral stem in accordance with one or more features of the present disclosure.
Figure 2B:
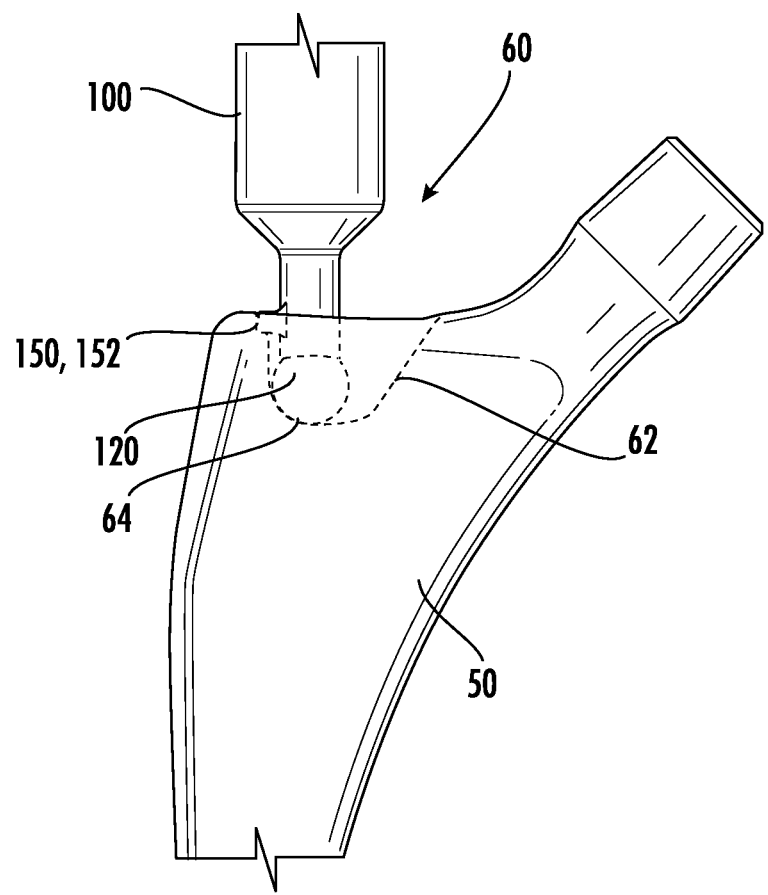

As previously mentioned, alternative coupling or connection mechanisms may be used to couple the inserter 100 to the femoral stem 50. For example, referring to FIGS. 2A and 2B, in one embodiment, the ball-shaped head portion 120 may include a key or a projection 150 such as, for example, a laterally extending projection that is arranged and configured to engage a corresponding recess 152 formed in the pocket 64 of the femoral stem 50. Thus arranged, when the ball-shaped head portion 120 is fully positioned within the pocket 64 of the femoral stem 50, the corresponding projection 150 and recess 152 prevent rotation of the inserter 100 relative to the femoral stem 50. The inserter 100 may be prevented from rotating about the femoral stem 50 in the Z-axis while enabling the user to still angularly adjust the position of the inserter 100 relative to the femoral stem 50 in one of the medial and lateral direction. Thus arranged, the inserter 100 may be coupled to the femoral stem 50 via a non-threaded, quick connect coupling mechanism.

Figure 3A:
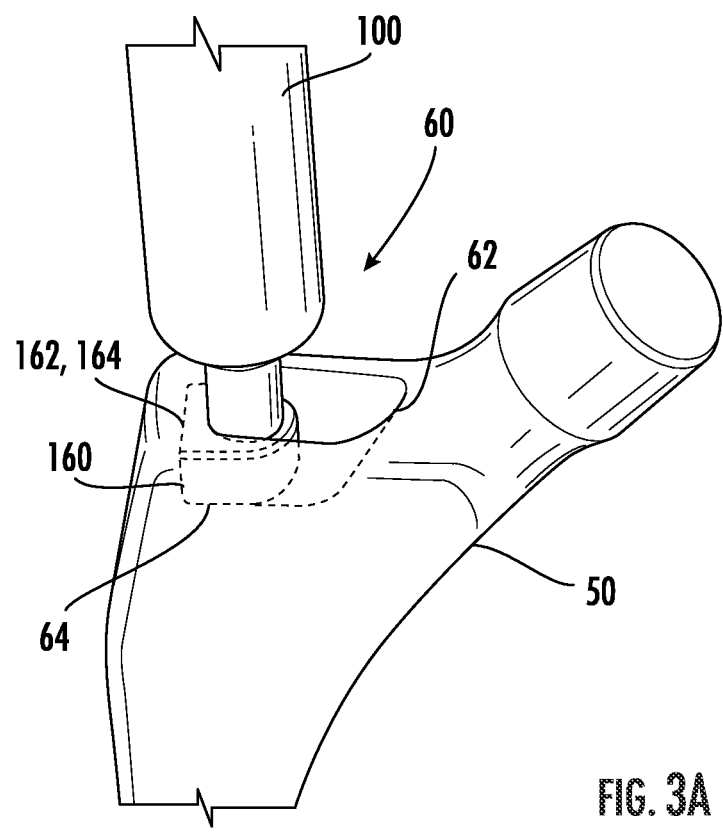
FIGS. 3A-3C illustrate various views of another example embodiment of an inserter being coupled to a femoral stem in accordance with one or more features of the present disclosure.
Figure 3B:
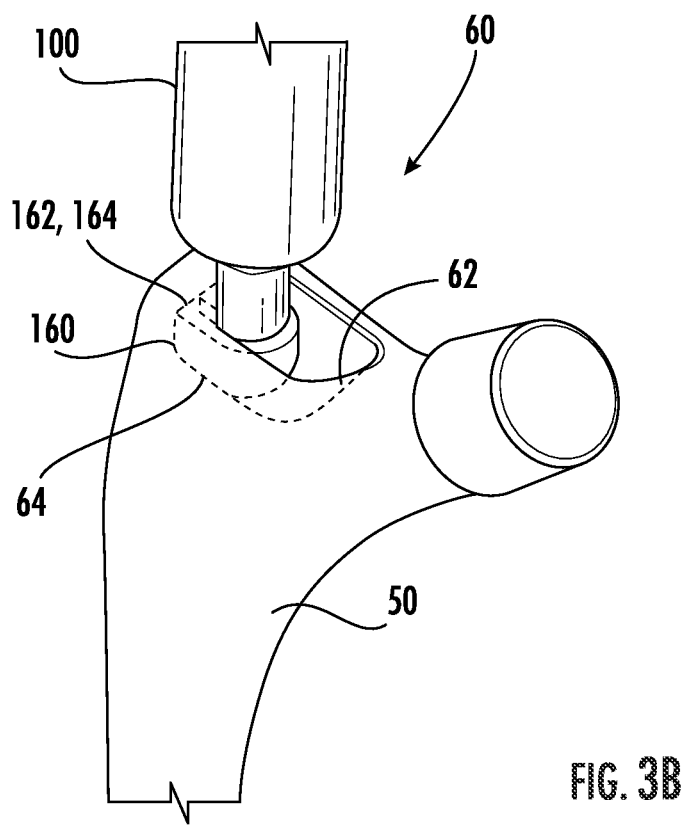
Figure 3C:
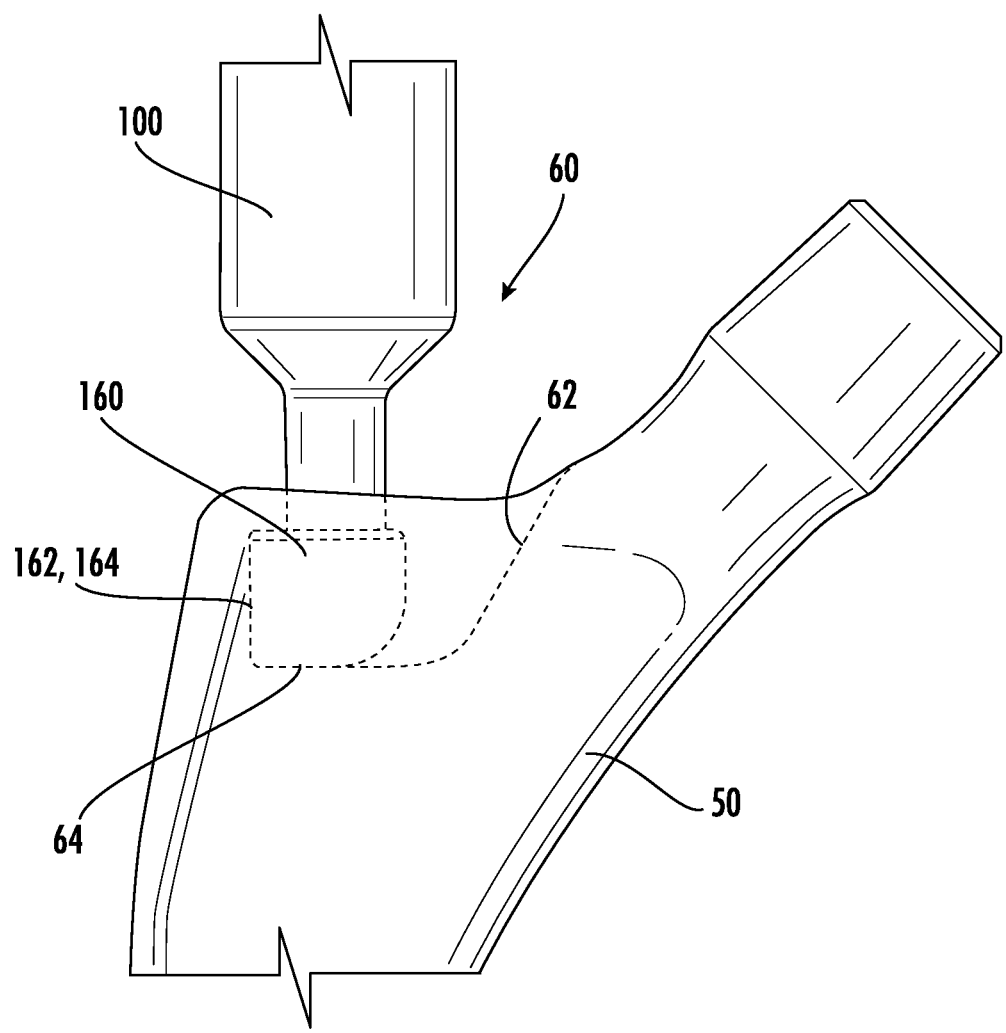

Referring to FIGS. 3A-3C, in one embodiment, the ball-shaped head portion 120 may be replaced with a semi-round or half-round head portion 160. For example, as illustrated, the half-round head portion 160 may include a straight lateral side surface 162. In use, when the half-round head portion 160 is properly positioned, the straight lateral side surface 162 contacts a corresponding surface 164 formed in the pocket 64 thereby preventing rotation of the inserter 100 relative to the femoral stem 50. The inserter 100 may be prevented from rotating about the femoral stem 50 in the Z-axis while enabling the user to still angularly adjust the position of the inserter 100 relative to the femoral stem 50 in one of the medial and lateral direction. Thus arranged, the inserter 100 may be coupled to the femoral stem 50 via a non-threaded, quick connect coupling mechanism.

Figure 4A:
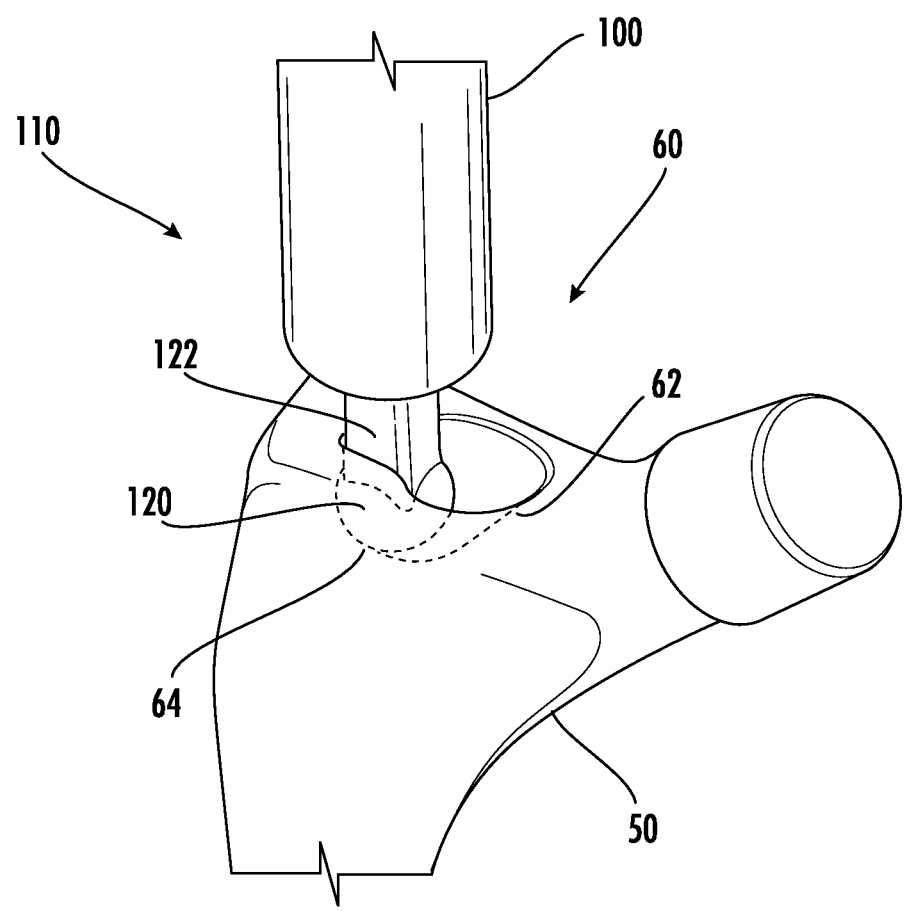
FIGS. 4A and 4B illustrate various views of another example embodiment of an inserter being coupled to a femoral stem in accordance with one or more features of the present disclosure.
Figure 4B:
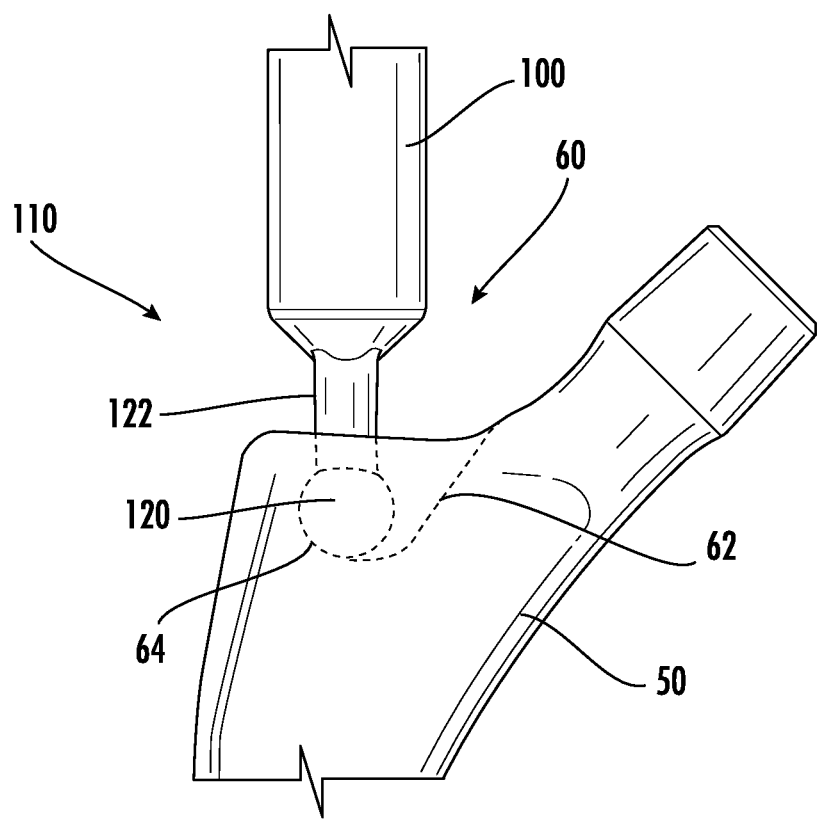

Referring to FIGS. 4A and 4B, in one embodiment, the extension or rod 122 extending at the distal end 110 of the inserter 100 may include a square or substantially square cross-sectional profile. Thus arranged, when the ball-shaped head portion 120 is fully positioned within the pocket 64 of the femoral stem 50, the corresponding square-shaped cross-sectional area of the extension or rod 122 and the corresponding shape of the pocket 64 prevents rotation of the inserter 100 relative to the femoral stem 50. The inserter 100 may be prevented from rotating about the femoral stem 50 in the Z-axis while enabling the user to still angularly adjust the position of the inserter 100 relative to the femoral stem 50 in one of the medial and lateral direction. Thus arranged, the inserter 100 may be coupled to the femoral stem 50 via a non-threaded, quick connect coupling mechanism.

Figure 5A:
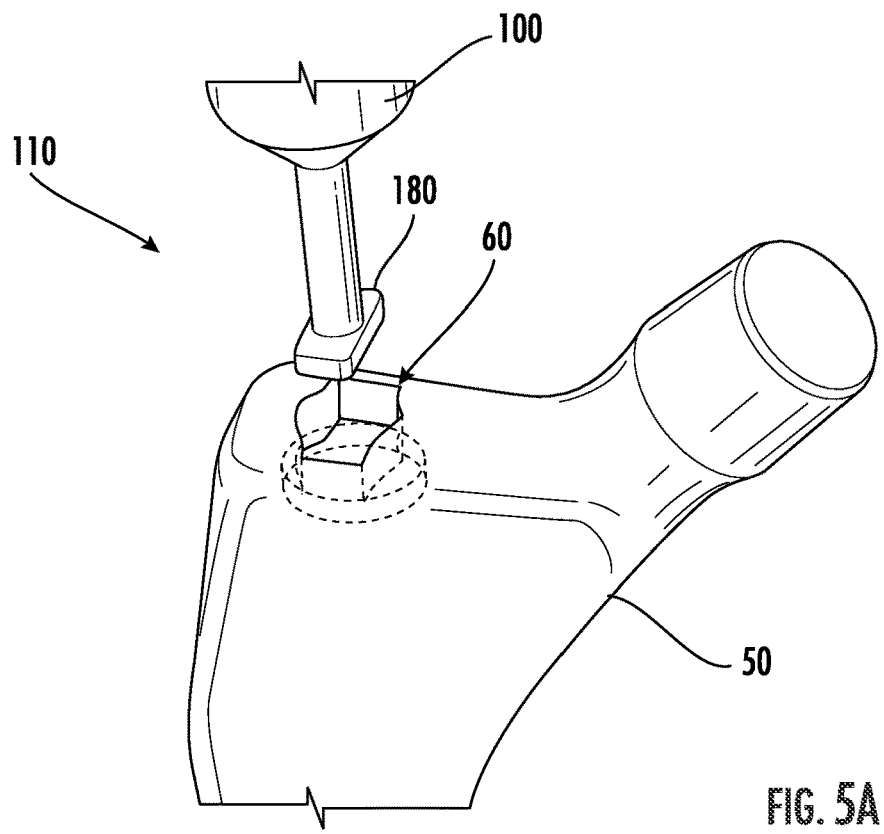
FIGS. 5A-5C illustrate various views of another example embodiment of an inserter being coupled to a femoral stem in accordance with one or more features of the present disclosure.
Figure 5B:
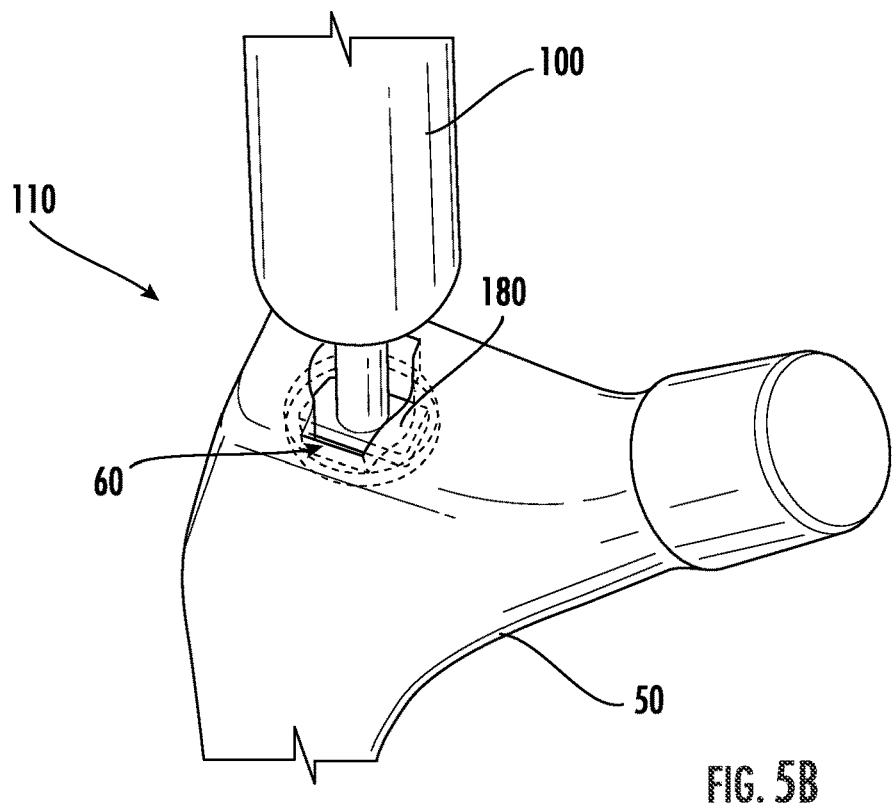
Figure 5C:
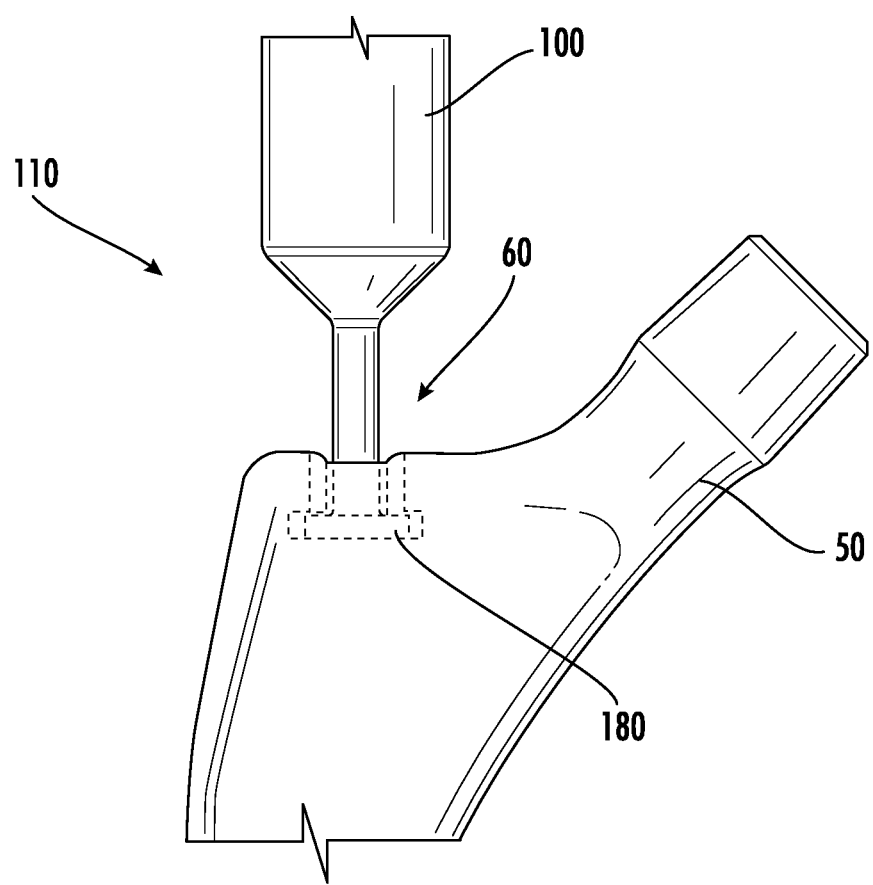

Referring to FIGS. 5A-5C, in one embodiment, the distal end 110 of the inserter 100 may include a T-shaped coupler 180. Similarly, the cavity 60 may be correspondingly shaped so that, in use, the T-shaped distal end of the inserter 100 may be inserted into the cavity 60 in a first position (FIG. 5A). Thereafter, the inserter 100 may be rotated by, for example, ninety-degrees, to fixedly couple the inserter 100 to the femoral stem 50. Thus arranged, the inserter 100 may be coupled to the femoral stem 50 via a non-threaded, quick connect coupling mechanism. In addition, the inserter 100 may be prevented from rotating about the femoral stem 50 in the Z-axis while enabling the user to still angularly adjust the position of the inserter 100 relative to the femoral stem 50 in one of the medial and lateral direction.

The foregoing description has broad application. While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments. Rather these embodiments should be considered as illustrative and not restrictive in character. All changes and modifications that come within the spirit of the invention are to be considered within the scope of the disclosure. The present disclosure should be given the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art. Unless otherwise defined, all technical terms used herein have the same meaning as commonly understood by one of ordinary skill in the art to which the disclosure belongs.

Directional terms such as top, bottom, superior, inferior, medial, lateral, anterior, posterior, proximal, distal, upper, lower, upward, downward, left, right, longitudinal, front, back, above, below, vertical, horizontal, radial, axial, clockwise, and counterclockwise) and the like may have been used herein. Such directional references are only used for identification purposes to aid the reader's understanding of the present disclosure. For example, the term "distal" may refer to the end farthest away from the medical professional/ operator when introducing a device into a patient, while the term "proximal" may refer to the end closest to the medical professional when introducing a device into a patient. Such directional references do not necessarily create limitations, particularly as to the position, orientation, or use of this disclosure. As such, directional references should not be limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

It should be understood that, as described herein, an "embodiment" (such as illustrated in the accompanying Figures) may refer to an illustrative representation of an environment or article or component in which a disclosed concept or feature may be provided or embodied, or to the representation of a manner in which just the concept or feature may be provided or embodied. However, such illustrated embodiments are to be understood as examples (unless otherwise stated), and other manners of embodying the described concepts or features, such as may be understood by one of ordinary skill in the art upon learning the concepts or features from the present disclosure, are within the scope of the disclosure. Furthermore, references to "one embodiment" of the present disclosure are not intended to be interpreted as excluding the existence of additional embodiments that also incorporate the recited features.

In addition, it will be appreciated that while the Figures may show one or more embodiments of concepts or features together in a single embodiment of an environment, article, or component incorporating such concepts or features, such concepts or features are to be understood (unless otherwise specified) as independent of and separate from one another and are shown together for the sake of convenience and without intent to limit to being present or used together. For instance, features illustrated or described as part of one embodiment can be used separately, or with another embodiment to yield a still further embodiment. Thus, it is intended that the present subject matter covers such modifications and variations as come within the scope of the appended claims and their equivalents.

As used herein, an element or step recited in the singular and proceeded with the word "a" or "an" should be understood as not excluding plural elements or steps, unless such exclusion is explicitly recited. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

The phrases "at least one", "one or more", and "and/or", as used herein, are open-ended expressions that are both conjunctive and disjunctive in operation. The terms "a" (or "an"), "one or more" and "at least one" can be used interchangeably herein.

Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The drawings are for purposes of illustration only and the dimensions, positions, order and relative to sizes reflected in the drawings attached hereto may vary.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments or configurations. Moreover, the following claims are hereby incorporated into this Detailed Description by this reference, with each claim standing on its own as a separate embodiment of the present disclosure.

The invention claimed is:

1. An orthopedic system for total hip arthroplasty, the orthopedic system comprising:
 a femoral stem; and
 an inserter arranged and configured to couple to the femoral stem to facilitate insertion of the femoral stem within an intramedullary canal of a patient's bone, the inserter including a quick-connect, non-threaded connection for coupling the femoral stem;
 wherein the femoral stem includes a cavity comprising a ramped pathway in communication with a pocket, the inserter includes an enlarged head portion comprising a ball-shaped head portion extending from a distal end of the inserter, the head portion being arranged and configured to be received within the cavity of the femoral stem to couple the inserter to the femoral stem while enabling an orientation of the inserter to be angularly adjustable relative to the femoral stem, the ramped pathway being arranged and configured to guide the ball-shaped head portion into the pocket.

2. The orthopedic system of claim 1, wherein, in use with the inserter coupled to the femoral stem, the inserter is arranged and configured to be angularly adjustable relative to the femoral stem.

3. The orthopedic system of claim 2, wherein, in use with the inserter coupled to the femoral stem, the inserter is arranged and configured to enable a medial-lateral position of the inserter to be adjusted relative to the femoral stem.

4. The orthopedic system of claim 2, wherein, in use with the inserter coupled to the femoral stem, the inserter is arranged and configured to enable a rotational position of the inserter in a Z-axis to be adjusted relative to the femoral stem.

5. The orthopedic system of claim 1, wherein the inserter includes a body portion and a reduced diameter rod extending from the body portion, the ball-shaped head portion being arranged at a distal end of the reduced diameter rod.

6. The orthopedic system of claim 1, wherein the ball-shaped head portion is inserted into the pocket by inserting the ball-shaped head portion along the ramped pathway until the ball-shaped head portion reaches a distal end of the ramped pathway and then moving the ball-shaped head portion laterally into the pocket.

7. The orthopedic system of claim 1, wherein the cavity is arranged and configured to prevent the ball-shaped head portion from being axially pulled out of the pocket.

8. The orthopedic system of claim 7, wherein the pocket includes an inwardly extending ledge arranged and configured to prevent the ball-shaped head portion from being axially pulled out of the pocket.

9. The orthopedic system of claim 7, wherein the pocket includes a smaller diameter cross-sectional area at a proximal end thereof arranged and configured to prevent the ball-shaped head portion from being axially pulled out of the pocket.

10. The orthopedic system of claim 7, wherein the ball-shaped head portion includes a key arranged and configured to engage a corresponding recess formed in the pocket of the femoral stem, engagement of the key and the recess preventing angular adjustment of the inserter relative to the femoral stem.

11. The orthopedic system of claim 1, wherein the enlarged head portion comprises a semi-round head portion including a straight lateral side surface for interacting with a straight surface formed in the pocket, interaction between the straight lateral side surface and the straight surface preventing angular adjustment of the inserter relative to the femoral stem.

12. The orthopedic system of claim 1, wherein the enlarged head portion comprises a T-shaped end portion, the femoral stem includes a corresponding cavity arranged and configured to receive the T-shaped end portion.

13. The orthopedic system of claim 1, wherein the inserter includes a body portion and an extension rod extending from the body portion, the enlarged head portion being arranged at a distal end of the rod, the extension rod including a square cross-sectional profile, the extension rod being arranged and configured to interact with the pocket to prevent angular adjustment of the inserter relative to the femoral stem.

14. A method for coupling an orthopedic inserter to a femoral stem, the method comprising:
  inserting a ball-shaped head portion formed at a distal end of the orthopedic inserter into a cavity formed in the femoral stem, wherein inserting the ball-shaped head portion into the cavity includes:
    positioning the ball-shaped head portion into the cavity adjacent to a ramped pathway;
    inserting the ball-shaped head portion into the cavity along the ramped pathway;
    laterally moving the ball-shaped head portion into a pocket of the cavity; and
    tilting the inserter relative to the femoral stem.

15. The method of claim 14, wherein the pocket includes a ledge extending therein, the ledge being arranged and configured to prevent the ball-shaped head portion from being axially pulled out of the pocket.

16. The method of claim 15, wherein inserting the ball-shaped head portion into the cavity along the ramped pathway includes positioning the ball-shaped head portion distally, beneath the ledge.

17. The method of claim 15, wherein laterally moving the ball-shaped head portion into the pocket includes laterally moving the ball-shaped head portion laterally beneath the ledge.

18. The method of claim 17, further comprising decoupling the inserter from the femoral stem via laterally moving the ball-shaped head portion from beneath the ledge toward the ramped pathway and axially withdrawing the ball-shaped head portion from the cavity along the ramped pathway.

* * * * *